United States Patent
Amako et al.

(10) Patent No.: US 6,172,252 B1
(45) Date of Patent: Jan. 9, 2001

(54) PHENO-FUNCTIONAL ORGANOSILICON COMPOUNDS AND METHOD FOR THE PREPARATION

(75) Inventors: Masaaki Amako; Tadashi Okawa, both of Chiba Prefecture (JP)

(73) Assignee: Dow Corning Toray Silicone Co., Ltd., Tokyo (JP)

(*) Notice: Under 35 U.S.C. 154(b), the term of this patent shall be extended for 0 days.

(21) Appl. No.: 09/531,935

(22) Filed: Mar. 21, 2000

(30) Foreign Application Priority Data

Mar. 31, 1999 (JP) .................................. 11-090576

(51) Int. Cl.$^7$ ................................. C07F 7/08; C07F 7/18
(52) U.S. Cl. ............................................. 556/449; 556/445
(58) Field of Search ..................... 556/445, 449

(56) References Cited

U.S. PATENT DOCUMENTS

| | | | |
|---|---|---|---|
| 3,576,032 | * 4/1971 | Pearce | 556/449 |
| 3,622,609 | 11/1971 | Mironov et al. | 260/448.2 E |
| 4,948,888 | * 8/1990 | Greco et al. | 556/449 |
| 5,130,460 | 7/1992 | Kamei et al. | 556/449 |
| 5,349,096 | 9/1994 | Cockman et al. | 568/896 |
| 5,532,400 | * 7/1996 | Parker et al. | 556/449 |

FOREIGN PATENT DOCUMENTS

| | | |
|---|---|---|
| 62-275116 | 11/1987 | (JP) . |
| 2-166123 | 6/1990 | (JP) . |
| 2-225524 | 9/1990 | (JP) . |
| 61-84022 | 7/1994 | (JP) . |
| 10-259258 | 9/1998 | (JP) . |
| 10-294580 | 11/1998 | (JP) . |

* cited by examiner

*Primary Examiner*—Paul F. Shaver
(74) *Attorney, Agent, or Firm*—Larry A. Milco

(57) ABSTRACT

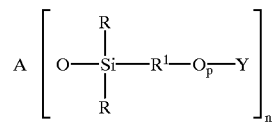

wherein A is hydrogen or a residue afforded by the removal of n hydroxyl groups from an m-valent alcohol, each R is independently a monovalent hydrocarbon group free of aliphatic unsaturation, each $R^1$ is independently a divalent hydrocarbon group containing at least 2 carbon atoms, m and n are natural numbers wherein m≧n, p is 0 or 1, and Y is a phenol group having the formula:

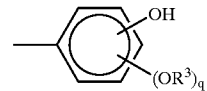

wherein $R^3$ is alkyl and q is from 0 to 4. Also, a method of preparing a phenol-functional organosilicon compound.

19 Claims, No Drawings

PHENO-FUNCTIONAL ORGANOSILICON COMPOUNDS AND METHOD FOR THE PREPARATION

FIELD OF THE INVENTION

The present invention relates to phenol group-containing organosilicon compounds, hereinafter referred to as phenol-functional organosilicon compounds, and to a method for the preparation thereof.

BACKGROUND OF THE INVENTION

A number of phenol-functional organosilicon compounds and methods for their synthesis are known. For example, U.S. Pat. No. 3,622,609 teaches a method for the synthesis of 1,3-bis-γ-(ortho-hydroxyphenyl)propyl- 1,1,3,3-tetramethyldisiloxane by the dimethylsilylation of the hydroxyl group in 2-allylphenol, hydrosilylation polymerization of the reaction product, and then ring opening with sodium hydroxide followed by treatment with sulfuric acid. However, this method cannot provide compounds containing both a phenol group and a functional group other than a phenol group. Japanese Laid Open (Kokai or Unexamined) Patent Application Numbers Hei 2-166123 (166,123/1990) and Hei 2-225524 (225,524/1990) describe a method for synthesizing phenol-functional organosiloxanes by carrying out an addition reaction between an SiH-functional organosiloxane and tert-butoxystyrene (phenolic hydroxyl protected by the tert-butyl group) followed by de-tert-butylation in the presence of a strong acid. This method is, however, unable to produce compounds that contain the phenol group and alkenyl in the same molecule and also suffers from the disadvantage that the siloxane chain is susceptible to cleavage by the strong acid. Otherwise, Japanese Laid Open (Kokai or Unexamined) Patent Application Numbers Sho 62-275116 (275,116/1987) and Sho 61-84022 (84,02211986) describe phenol-functional silanes, but these compounds are limited to phenol-functional trialkylsilanes and do not include alkoxysilyl-functional or silanol-functional species. Moreover, the synthetic methods disclosed therein are very complex and do not provide high yields.

The present inventors have already disclosed organosiloxanes that contain both alkenyl and the phenol group as well as a method for the synthesis thereof (Japanese Patent Application Number Hei 10-294580 (294,580/1998)). Unfortunately, this method carries with it the risk that the alkenyl group-containing organosiloxane product will polymerize during the purification phase. In addition, this method cannot be used to synthesize compounds that contain both the phenol group and alkoxysilyl group or silanol group in the same molecule.

SUMMARY OF THE INVENTION

In specific terms, an object of this invention is to provide novel phenol-functional organosilicon compounds containing both a phenol group and alkoxysilyl, alkenyl, or silanol group in the same molecule. An additional object of this invention is to provide a method for preparing the novel phenol-functional organosilicon compounds.

The present invention is directed to a phenol-functional organosilicon compound having the formula:

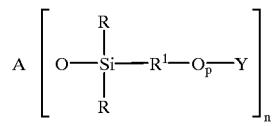

wherein A is hydrogen or a residue afforded by the removal of n hydroxyl groups from an m-valent alcohol, each R is independently a monovalent hydrocarbon group free of aliphatic unsaturation, each $R^1$ is independently a divalent hydrocarbon group containing at least 2 carbon atoms, m and n are natural numbers wherein $m \geq n$, p is 0 or 1, and Y is a phenol group having the formula:

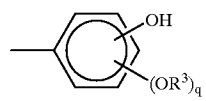

wherein $R^3$ is alkyl and q is from 0 to 4.

The present invention is also directed to a method of preparing a phenol-functional organosilicon compound, said method comprising the steps of:

(A) reacting an aliphatically unsaturated SiH-functional organosilicon compound in the presence of a hydrosilylation catalyst to form an addition reaction product, wherein the SiH-functional organosilicon compound has the formula:

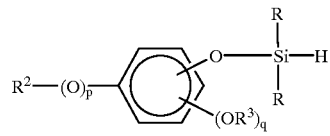

wherein each R is independently a monovalent hydrocarbon group free of aliphatic unsaturation, $R^2$ is an aliphatically unsaturated monovalent hydrocarbon group, $R^3$ is alkyl, p is 0 or 1, and q is from 0 to 4; and (B) reacting the addition reaction product with an alcohol or water to produce a phenol-functional organosilicon compound, wherein the alcohol has the formula $A(OH)_n$ wherein A is hydrogen or a residue afforded by the removal of n hydroxyl groups from an m-valent alcohol and m and n are natural numbers wherein $m \geq n$.

The phenol-functional organosilicon compounds of this invention contain both a phenol group and an alkoxysilyl, alkenyl, or silanol group in the same molecule. As a result, curable silicone compositions containing these phenol-functional organosilicon compound have excellent adhesion to glasses, organic resins such as phenolic resins and epoxy resins, and metals such as copper, aluminum, and stainless steel. The method of this invention is a highly productive method for producing the novel phenol-functional organosilicon compound.

The phenol-functional organosilicon compound of this invention can be used as adhesion promoters in curable silicone compositions. In particular the phenol-functional organosilicon compound of the instant invention is highly suitable for use as an adhesion promoter in addition reaction-curing silicone compositions. The phenol-functional organosilicon compound of this invention can also be used as an optical matching oil and as a polymerization terminator.

DETAILED DESCRIPTION OF THE INVENTION

A phenol-functional organosilicon compound according to the present invention has the formula:

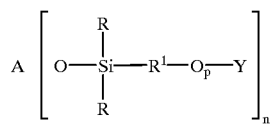

wherein A is hydrogen or a residue afforded by the removal of n hydroxyl groups from an m-valent alcohol, each R is independently a monovalent hydrocarbon group free of aliphatic unsaturation, each $R^1$ is independently a divalent hydrocarbon group containing at least 2 carbon atoms, m and n are natural numbers wherein $m \geq n$, p is 0 or 1, and Y is a phenol group having the formula:

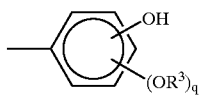

wherein $R^3$ is alkyl and q is from 0 to 4.

In the formula of the phenol-functional organosilicon compound of the present invention, the subscripts m and n are typically in the range from 1 to 5, and m must be greater than or equal to n.

Examples of alcohol-derived residues represented by A include, but are not limited to, the following monovalent, divalent, and trivalent groups: unsubstituted hydrocarbyl, alkyloxyalkylene, alkenyloxyalkylene, phenyloxyalkylene, hydroxy-functional hydrocarbyl, hydroxy-functional alkyloxyalkylene, and hydroxy-functional alkenyloxyalkylene. The following are examples of residues afforded by removal of the hydroxyl group from a monovalent alcohol: methyl, ethyl, propyl, butyl, hexyl, allyl, butenyl, hexenyl, and propylene oxide. Residues afforded by the removal of 1 hydroxyl group from a divalent alcohol are exemplified by 2-hydroxyethyl, 2-hydroxypropyl, 3-hydroxypropyl, 2-hydroxybutyl, 3-hydroxybutyl, and 3-allyloxy-2-hydroxypropyl. Residues afforded by the removal of 2 hydroxyl groups from a divalent alcohol are exemplified by ethylene, propylene, butylene, hexylene, and ethyleneoxypropylene. Residues afforded by the removal of 1 hydroxyl group from a trivalent alcohol are exemplified by dihydroxypropyl, dihydroxybutyl, and dihydroxyhexyl. Residues afforded by the removal of 2 hydroxyl groups from a trivalent alcohol are exemplified by hydroxypropylene, hydroxybutylene, and hydroxyhexylene.

Preferred embodiments of the group A are as follows: the hydrogen atom; alkyl such as methyl and ethyl and aliphatically unsaturated groups such as allyl, butenyl, and hexenyl among the residues afforded by removal of the hydroxyl group from a monovalent alcohol; and hydroxyl-functional alkenyloxyalkylene groups such as 3-allyloxy-2-hydroxypropyl among the residues afforded by removal of 1 hydroxyl group from a divalent alcohol. Aliphatically unsaturated groups are particularly preferred from the perspective of their adhesion-promoting performance.

Examples of the monovalent hydrocarbon groups represented by R include, but not limited to, alkyl such as methyl, ethyl, butyl, pentyl, and hexyl; aryl such as phenyl, tolyl, and xylyl; and aralkyl such as benzyl and phenethyl. Examples of the divalent hydrocarbon groups represented by $R^1$ include, but not limited to, alkylene groups such as ethylene, propylene, butylene, and hexylene and by arylene groups such as phenylene.

In the phenol group represented by Y, the bonding positions of the hydroxyl and alkoxy are not critical. Examples of phenol groups include, but are not limited to, 2-hydroxyphenyl, 4-hydroxyphenyl, 4-hydroxy-3-methoxyphenyl, and 3,5-dimethoxy-4-hydroxyphenyl. Preferably, Y is 2-hydroxyphenyl or 4-hydroxy-3-methoxyphenyl, based on availability. The subscript q is typically 0 or 1.

Examples of alkyl groups represented by $R^3$ in the formula of the phenol group include, but are not limited to, methyl, ethyl, propyl, and butyl with methyl being specifically preferred.

Examples of the phenol-functional organosilicon compounds of this invention include, but are not limited to, the following silanes:

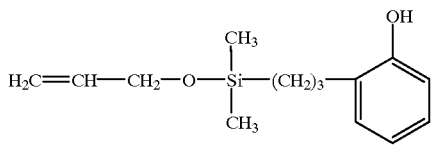

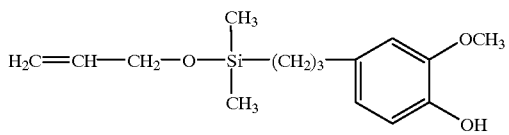

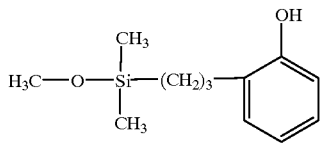

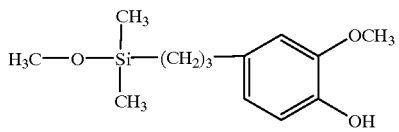

-continued
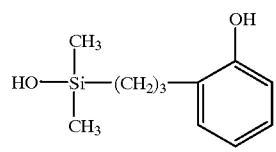
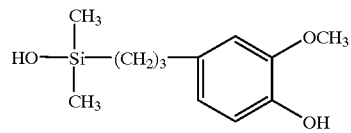
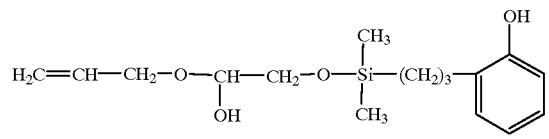
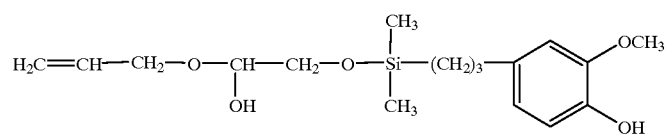
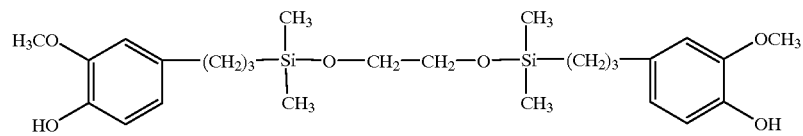
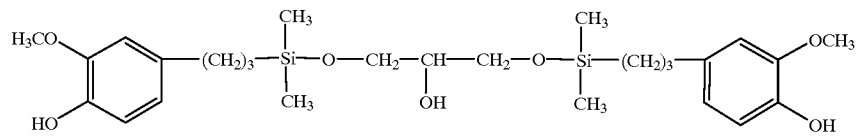
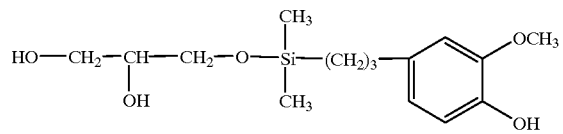
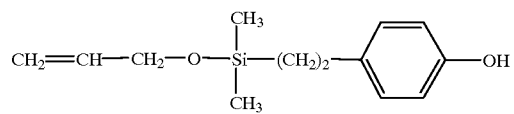
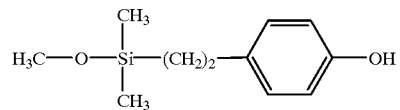
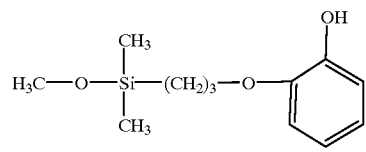
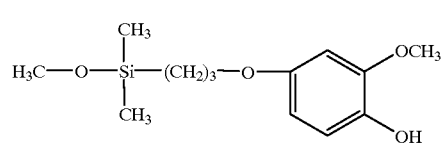
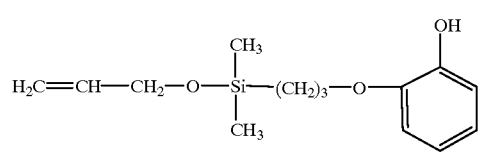

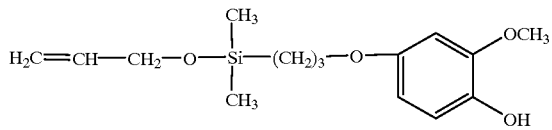

-continued

The phenol-functional organosilicon compounds of this invention can be synthesized, for example, by an intramolecular or intermolecular addition reaction of an aliphatically unsaturated SiH-functional organosilicon compound in the presence of a hydrosilylation catalyst. In particular, a method of preparing a phenol-functional organosilicon compound according to the present invention comprises the steps of:

(A) reacting an aliphatically unsaturated SiH-functional organosilicon compound in the presence of a hydrosilylation catalyst to form an addition reaction product, wherein the SiH-functional organosilicon compound has the formula:

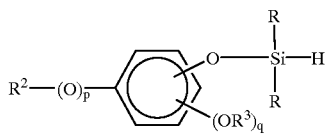

wherein each R is independently a monovalent hydrocarbon group free of aliphatic unsaturation, $R^2$ is an aliphatically unsaturated monovalent hydrocarbon group, $R^3$ is alkyl, p is 0 or 1, and q is from 0 to 4; and (B) reacting the addition reaction product with an alcohol or water to produce a phenol-functional organosilicon compound, wherein the alcohol has the formula $A(OH)_n$ wherein A is hydrogen or a residue afforded by the removal of n hydroxyl groups from an m-valent alcohol and m and n are natural numbers wherein $m \geq n$.

Examples of aliphatically unsaturated monovalent hydrocarbon groups represented by $R^2$ in the preceding formula include, but are not limited to, vinyl, allyl, butenyl, and hexenyl. Allyl is preferred based on cost and availability. Preferred SiH-functional organosilicon compounds are the dimethylsilyl ether of 2-allylphenol and the dimethylsilyl ether of eugenol. A, R, $R^3$, m, n, p, and q are as defined and exemplified above for the phenol-functional organosilicon compound of the present invention.

The hydrosilylation catalyst of the present method can be, for example, a catalytic complex of a transition metal from Group 8 of the Periodic Table. Platinum-based catalysts are particularly effective within this group of catalysts and are specifically exemplified by platinum compounds such as chloroplatinic acid and its alcohol solutions, olefin complexes of platinum, and platinum/vinyl-functional siloxane complexes. These catalysts are used in sufficient quantity to give 0.001 to 10,000 and more preferably 0.1 to 100 weight parts platinum metal for each one million weight parts of the SiH-functional organosilicon compound and the alcohol or water combined.

Examples of alcohols suitable for use in the present method include, but re not limited to, allyl alcohol, glycerol α-monoallyl ether, methanol, ethanol, propanol, and ethylene glycol. The alcohol or water used in step (B) of the present method is used in sufficient quantity such that the ratio of the number of equivalents of OH in the alcohol or water per equivalent of silyl phenyl ether group in the SiH-functional organosilicon compound is at least 1.0, preferably from 1.0 to 50, and more preferably from 1.5 to 10.

Since the intramolecular and intermolecular addition reactions of the SiH-functional organosilicon compound are exothermal, in order to prevent sudden heating the method of the present invention is preferably carried out by first mixing the hydrosilylation catalyst with a solvent to form a mixture and then gradually adding the SiH-functional organosilicon compound dropwise to the mixture. Solvents usable for this purpose are exemplified by aromatic solvents such as benzene, toluene, and xylene; aliphatic solvents such as pentane, hexane, heptane, octane, and decane; ethers such as tetrahydrofuran, diethyl ether, and dibutyl ether; ketones such as acetone and methyl ethyl ketone; esters such as ethyl acetate and butyl acetate; and chlorinated hydrocarbons such as carbon tetrachloride, trichloroethane, methylene dichloride, and chloroform. The reaction can be run at room temperature, but in general it is preferable, from the standpoint of the reaction rate, to run the reaction at from 50 to 200° C. During the course of the reaction, the reaction mixture can be analyzed, for example, by gas chromatography (GLC) or infrared spectroscopic analysis (IR) and the reaction can be considered as complete when, for example, the absorption characteristic of the silicon-bonded hydrogen in the SiH-functional organosilicon compound has more or less completely disappeared. The water or alcohol is then added to the resulting addition reaction product, resulting in a desilylation reaction. Although the desilylation reaction can be carried out using methods known in the art, alcohol exchange by heating in the presence of a basic catalyst, e.g., an amine, etc., will produce the desired organosilicon compound in high yields without the occurrence of side reactions (Japanese Patent Application Number Hei 10-259258 (259, 258/1998)). After completion of the desilylation reaction, the phenol-functional organosilicon compound of this invention can be recovered by removal of low boiling materials such as unreacted water or alcohol and solvent by, for example, distillation by heating at reduced pressure. It is preferable to purify the resulting organosilicon compound by distillation.

The phenol group present within the phenol-functional organosilicon compounds of this invention reacts readily with a variety of functional groups. As a consequence, when an organosilicon compound of this invention is blended into a curable silicone composition and the composition is applied to a substrate and cured, the cured silicone strongly adheres to the substrate. This applies to a variety of substrates, for example, organic resins such as phenolic resins, epoxy resins, polybutylene terephthalate resins, and polycarbonate resins; metals such as copper, aluminum, and stainless steel; glasses; etc. The cured silicone also strongly adheres to thermosetting resins such as phenolic resins and epoxy resins.

The phenol-functional organosilicon compounds of this invention contain both a phenol group and an alkoxysilyl, alkenyl, or silanol group in the same molecule. As a result, curable silicone compositions containing these phenol-functional organosilicon compounds have excellent adhesion to glasses, organic resins such as phenolic resins and epoxy resins, and metals such as copper, aluminum, and stainless steel. The method of this invention is a highly productive method for producing the novel phenol-functional organosilicon compounds.

The phenol-functional organosilicon compounds of this invention can be used as adhesion promoters in curable silicone compositions. In particular the phenol-functional organosilicon compounds of the instant invention are highly suitable for use as adhesion promoters in addition reaction-curing silicone compositions. The phenol-functional organosilicon compounds of this invention can also be used as optical matching oil and as polymerization terminator.

EXAMPLES

The following examples are presented to further illustrate the phenol-functional organosilicon compounds and method of the present invention, which is delineated in the claims.

Reference Example 1

10.0 g (75.0 mmol) 1,1,3,3-tetramethyldisilazane and 16.4 g (99.9 mmol) eugenol were introduced into a 100-mL three-neck flask equipped with a thermometer, condenser, and addition funnel. The contents were stirred for 1 hour at 80° C., at which point the GLC signal for eugenol had disappeared. The low boiling materials were then distilled from the reaction mixture using an aspirator to give 19.9 g of a colorless and transparent liquid. Analysis of this liquid by nuclear magnetic resonance analysis (NMR) and IR confirmed it to be an allyl- and SiH-functional silane having the formula:

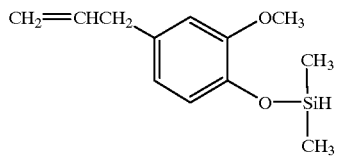

The purity of this silane by GLC was 98%.

Reference Example 2

10.0 g (75.0 mmol) 1,1,3,3-tetramethyldisilazane and 8.4 g (62.6 mmol) 2-allylphenol were introduced into a 100-mL three-neck flask equipped with a thermometer, condenser, and addition funnel. The contents were stirred for 1 hour at 80° C., at which point the GLC signal for 2-allylphenol had disappeared. The low boiling materials were then distilled from the reaction mixture using an aspirator to give 11.8 g of a colorless and transparent liquid. Analysis of this liquid by NMR and IR confirmed it to be an allyl- and SiH-functional silane having the formula:

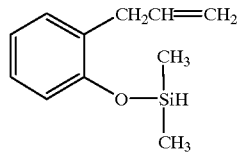

The purity of this silane by GLC was 98%.

Example 1

Into a 300-mL four-neck flask equipped with a reflux condenser, thermometer, addition funnel, and stirring paddle were introduced 100 g toluene and 50 μL of a toluene solution (platinum metal concentration=2 weight%) of a platinum/vinylsiloxane complex produced from chloroplatinic acid and 1,3-divinyltetramethyldisiloxane. The contents were heated to 90° C. and 113.80 g (0.4774 mol) of the silane synthesized as described in Reference Example 1 was then added dropwise. After the completion of silane addition, the reaction was stirred for an additional 3 hours at 100° C., at which point the reaction was taken as complete because analysis of the reaction solution by IR showed that the SiH signal had almost completely disappeared. The reaction solution was then transferred to a 500-mL four-neck flask equipped with a reflux condenser, thermometer, and stirring paddle, followed by the addition thereto of 101 g allyl alcohol, 40 g tetrahydrofuran, and 20 mL diethylamine and stirring for 14 hours at 90° C. After stirring had ended, the low boiling materials were distilled from the reaction solution by heating under reduced pressure to give 116.50 g of a reaction product. Analysis of this reaction product by NMR and IR confirmed it to be a phenol-functional propenoxysilane having the formula:

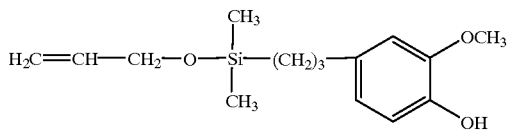

The purity of this silane by GLC was 93.4%.

Example 2

Into a 300-mL four-neck flask equipped with a reflux condenser, thermometer, addition funnel, and stirring paddle were introduced 100 g toluene and 35 μL of a toluene solution (platinum metal concentration=2 weight%) of a platinum/vinylsiloxane complex produced from chloroplatinic acid and 1,3-divinyltetramethyldisiloxane. The contents were heated to 90° C. and 40.00 g (179.9 mmol) of the silane synthesized as described in Reference Example 1 was then added dropwise. After the completion of silane addition, the reaction was stirred for an additional 5 hours at 100° C., at which point the reaction was taken as complete because analysis of the reaction solution by IR showed that the SiH signal had almost completely disappeared. At this point the toluene solution weighed 120.01 g. Analysis of this toluene solution by IR showed it to be a toluene solution of a reaction product formed by the intermolecular hydrosilylation polymerization of the silane in Reference Example 1, wherein the reaction product has the formula:

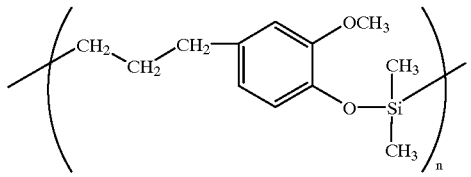

13.04 g of the toluene solution of this addition reaction product was then transferred to a 100-mL three-neck flask equipped with a reflux condenser and thermometer, followed by the addition thereto of 10.00 g glycerol α-monoallyl ether, 10 g tetrahydrofuran, and 2.0 mL diethylamine and stirring for 9 hours at 80 to 90° C. After stirring had ended, the low boiling materials were distilled from the reaction solution by heating under reduced pressure to give 4.587 g of a reaction product. Analysis of this reaction product by NMR and IR confirmed it to be a phenol-functional silane having the formula:

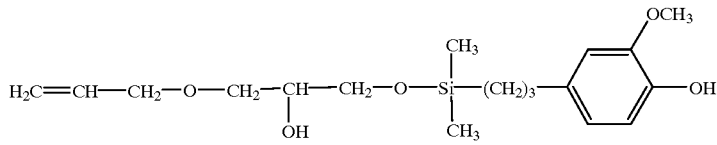

The purity of this silane by GLC was 80%. The remaining 20% was the starting glycerol α-monoallyl ether.

Example 3

Into a 300-mL four-neck flask equipped with a reflux condenser, thermometer, addition funnel, and stirring paddle were introduced 100 g toluene and 35 μL of a toluene solution (platinum metal concentration=2 weight%) of a platinum/vinylsiloxane complex produced from chloroplatinic acid and 1,3-divinyltetramethyldisiloxane. The contents were heated to 90° C. and 40.00 g (179.9 mmol) of the silane synthesized as described in Reference Example 1 was then added dropwise. After the completion of silane addition, the reaction was stirred for an additional 5 hours at 100° C., at which point the reaction was taken as complete because analysis of the reaction solution by IR showed that the SiH signal had almost completely disappeared. At this point the toluene solution weighed 120.01 g. Analysis of this toluene solution by IR showed it to be a toluene solution of a reaction product formed by the intermolecular hydrosilylation polymerization of the silane in Reference Example 1, wherein the reaction product has the formula:

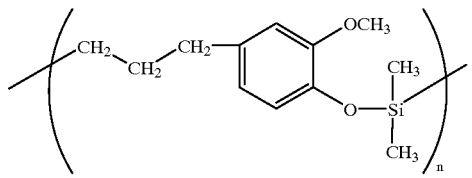

10.11 g of the toluene solution of this addition reaction product was then transferred to a 50-mL pear-shaped flask equipped with a reflux condenser, followed by the addition thereto of 10.12 g methanol, 5.00 g tetrahydrofuran, and 1.0 mL diethylamine and stirring for 8 hours while heating at an oil bath temperature of 108° C. After stirring had ended, the low boiling materials were distilled from the reaction solution by heating under reduced pressure to give 2.9471 g of a reaction product. Analysis of this reaction product by NMR and IR confirmed it to be a phenol-functional methoxysilane having the formula:

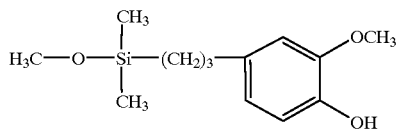

The purity of this silane by GLC was 94.9%.

Example 4

Into a 300-mL four-neck flask equipped with a reflux condenser, thermometer, addition funnel, and stirring paddle were introduced 100 g toluene and 35 μL of a toluene solution (platinum metal concentration=2 weight%) of a platinum/vinylsiloxane complex produced from chloroplatinic acid and 1,3-divinyltetramethyldisiloxane. The contents were heated to 90° C. and 40.00 g (179.9 mmol) of the silane synthesized as described in Reference Example 1 was then added dropwise. After the completion of silane addition, the reaction was stirred for an additional 5 hours at 100° C., at which point the reaction was taken as complete because analysis of the reaction solution by IR showed that the SiH signal had almost completely disappeared. At this point the toluene solution weighed 120.01 g. Analysis of this toluene solution by IR showed it to be a toluene solution of a reaction product formed by the intermolecular hydrosilylation polymerization of the silane in Reference Example 1, wherein the reaction product has the formula:

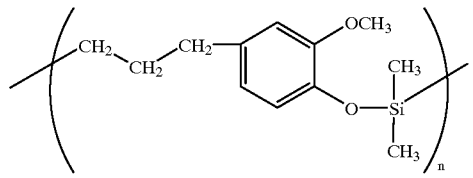

10.10 g of the toluene solution of this addition reaction product was then transferred to a 100-mL pear-shaped flask equipped with a reflux condenser, followed by the addition thereto of 20 g water, 10 g tetrahydrofuran, and 1.0 mL diethylamine and stirring for 8 hours while heating at an oil bath temperature of 108° C. After stirring had ended, the layers were separated and the recovered organic layer was washed with water, neutralized with acetic acid, again washed with water, and dried over sodium sulfate. After filtration to separate the drying agent, the low boiling materials were distilled from the reaction solution at room temperature under reduced pressure to give 2.46 g of a reaction product. Analysis of this reaction product by NMR and IR confirmed it to be a phenol-functional silanol having the formula:

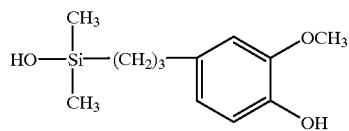

The purity of this silanol by GLC was 88%.

Example 5

Into a 300-mL four-neck flask equipped with a reflux condenser, thermometer, addition funnel, and stirring paddle were introduced 50 g toluene and 30 μL of a toluene solution (platinum metal concentration 2 weight%) of a platinum/vinylsiloxane complex produced from chloroplatinic acid and 1,3-divinyltetramethyldisiloxane. The contents were heated to 90° C. and 50.3 g (262 mmol) of the silane synthesized as described in Reference Example 2 was then added dropwise. After the completion of silane addition, the reaction was stirred for an additional 5 hours at 100° C., at which point the reaction was taken as complete because analysis of the reaction solution by IR showed that the SiH signal had almost completely disappeared. Distillation gave 44.8 g of a fraction at 65° C./3 mmHg. Analysis of this fraction by NMR and IR showed that the reaction product was an organosilicon compound formed by an intramolecular hydrosilylation reaction of the silane in Reference Example 2, wherein the organosilicon compound has the formula:

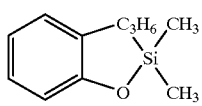

4.26 g of this organosilicon compound was introduced into a 50-mL pear-shaped flask equipped with a reflux condenser. This was followed by the addition of a stirring bar, 11.15 g allyl alcohol, and 1.00 g diethylamine and then stirring while heating for 7 hours at an oil bath temperature of 112° C. After stirring had ended, the reaction solution was transferred to a separatory funnel. Water and hexane were added, neutralization was carried out by the addition of acetic acid, and a water wash was carried out. This was followed by drying over sodium sulfate and filtration to remove the drying agent. Distillation of the lower boiling materials from the reaction solution by heating at reduced pressure then gave 1.664 g reaction product. Analysis of this reaction product by NMR and IR showed it to be a phenol-functional propenoxysilane having the formula:

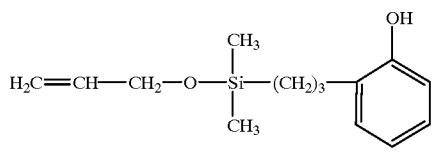

The purity of this silane by GLC was 67%. The remainder was the starting organosilicon compound as described above.

Example 6

A curable organopolysiloxane composition was prepared by mixing the following: 31.59 g (silicon-bonded hydrogen content=4.2 mmol, vinyl content=1.9 mmol) vinyldimethylsiloxy-endblocked dimethylsiloxane-methylhydrogensiloxane copolymer having the average formula:

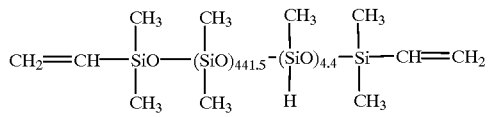

4.01 g hexamethyldisilazane-treated fumed silica (Aerosil 200BX from Nippon Aerosil), 5.5 mg phenylbutynol, 0.121 g (vinyl content=0.3 mmol)) of the reaction product of 3-glycidoxypropyltrimethoxysilane and silanol-endblocked dimethylsiloxane-methylvinylsiloxane copolymer, 4.42 g (vinyl content=15.8 mmol) of the phenol-functional organosilicon compound in Example 1 having the formula:

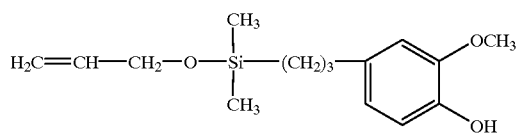

1.11 g trimethylsiloxy-endblocked methylhydrogenpolysiloxane (silicon-bonded hydrogen content=17.5 mmol), and a chloroplatinic acid/1,3-divinyltetramethyldisiloxane complex in sufficient quantity to provide 1.7 ppm platinum metal referred to the composition as a whole. The molar ratio in this composition of the Si-bonded hydrogen in the trimethylsiloxy-endblocked methylhydrogenpolysiloxane to the aliphatically unsaturated bond in the phenol-functional organosilicon compound was 1.2. The resulting curable organopolysiloxane composition was coated on a silicon chip (10 mm×10 mm×1 mm) so as to form a disk and was cured by holding for 30 minutes in a 180° C. oven. A curable epoxy resin composition was then applied so as to overcoat the cured silicone and was itself cured by holding for 1 hour in a 180° C. oven. This curable epoxy resin composition was composed of 50 parts Epotote YDF8170 from Toto Kasei Kabushiki Kaisha, 20 parts Novacure HX-3721 from Asahi Kasei Kogyo Kabushiki Kaisha, and 30 parts Noclac NS5 from Ouchi Shinko Kagaku Kogyo Kabushiki Kaisha. When the resulting cured product was inspected with an ultrasonic flaw detector, no debonding or delamination was observed at the respective interfaces formed by the epoxy resin, cured silicone, and silicon chip, nor at the interface where the three substances were in contact, and the cured silicone was thus confirmed to be tightly bonded.

Comparative Example 1

A curable organopolysiloxane composition was prepared as in Example 1, but in this case omitting the phenol-functional organosilicon. According to the method of Example 1, this composition was cured, epoxy resin was placed on the resulting cured product, and adhesion testing was carried out. In this case, however, delamination was observed at the epoxy resin/cured silicone interface, indicative of unsatisfactory adhesion of the cured That which is claimed is:

1. A phenol-functional organosilicon compound having the formula:

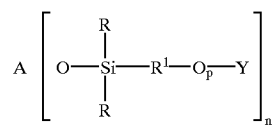

wherein A is hydrogen or a residue afforded by the removal of n hydroxyl groups from an m-valent alcohol, each R is independently a monovalent hydrocarbon group free of aliphatic unsaturation, each $R^1$ is independently a divalent hydrocarbon group containing at least 2 carbon atoms, m and n are natural numbers wherein m≧n, p is 0 or 1, and Y is a phenol group having the formula:

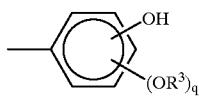

wherein R³ is alkyl and q is from 0 to 4.

2. The phenol-functional organosilicon compound according to claim 1, wherein A is hydrogen, alkyl, an aliphatically unsaturated group, or a hydroxyl-functional alkenyloxyalkylene group.

3. The phenol-functional organosilicon compound according to claim 2, wherein A is an aliphatically unsaturated group.

4. The phenol-functional organosilicon compound according to claim 1, wherein R³ is methyl.

5. The phenol-functional organosilicon compound according to claim 1, wherein m and n are each from 1 to 5.

6. The phenol-functional organosilicon compound according to claim 1, wherein q is 0 or 1.

7. A method of preparing a phenol-functional organosilicon compound, said method comprising the steps of:

(A) reacting an aliphatically unsaturated SiH-functional organosilicon compound in the presence of a hydrosilylation catalyst to form an addition reaction product, wherein the SiH-functional organosilicon compound has the formula:

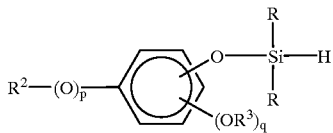

wherein each R is independently a monovalent hydrocarbon group free of aliphatic unsaturation, R² is an aliphatically unsaturated monovalent hydrocarbon group, R³ is alkyl, p is 0 or 1, and q is from 0 to 4; and (B) reacting the addition reaction product with an alcohol or water to produce a phenol-functional organosilicon compound, wherein the alcohol has the formula $A(OH)_n$ wherein A is hydrogen or a residue afforded by the removal of n hydroxyl groups from an m-valent alcohol and m and n are natural numbers wherein $m \geq n$.

8. The method according to claim 7, wherein A in the formula of the alcohol is hydrogen, alkyl, an aliphatically unsaturated group, or a hydroxyl-functional alkenyloxyalkylene group.

9. The method according to claim 8, wherein A in the formula of the alcohol is an aliphatically unsaturated group.

10. The method according to claim 7, wherein R³ is methyl.

11. The method according to claim 7, wherein m and n are each from 1 to 5.

12. The method according to claim 7, wherein q is 0 or 1.

13. The method according to claim 7, wherein the SiH-functional organosilicon compound is dimethylsilyl ether of allyl phenol or dimethylsilyl ether of eugenol.

14. The method according to claim 7, wherein the hydrosilylation catalyst is a platinum compound.

15. The method according to claim 7, wherein the alcohol is used in an amount such that the ratio of the number of equivalents of hydroxyl groups in the alcohol to the number of equivalents of silyl ether groups in the SiH-functional organosilicon compound is from 1.0 to 5.0.

16. The method according to claim 7, wherein the water is used in an amount such that the ratio of the number of equivalents of hydroxyl groups in the water to the number of equivalents of silyl ether groups in the SiH-functional organosilicon compound is from 1.0 to 5.0.

17. The method according to claim 7, wherein step (A) is carried out by first mixing the hydrosilylation catalyst with a solvent to form a mixture and then slowly adding the SiH-functional organosilicon compound dropwise to the mixture.

18. The method according to claim 7, wherein step (A) is carried out at from 50 to 200° C.

19. The method according to claim 7, further comprising the step of purifying the phenol-functional organosilicon compound by distillation.

* * * * *